US011691008B2

(12) United States Patent
Lee et al.

(10) Patent No.: US 11,691,008 B2
(45) Date of Patent: Jul. 4, 2023

(54) NEUROMIMETIC STIMULATING APPARATUS AND METHOD

(71) Applicant: Samsung Electronics Co., Ltd., Suwon-si (KR)

(72) Inventors: Hyungwoo Lee, Seoul (KR); Sang Joon Kim, Hwaseong-si (KR); JongPal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 935 days.

(21) Appl. No.: 16/115,907

(22) Filed: Aug. 29, 2018

(65) Prior Publication Data

US 2019/0091470 A1 Mar. 28, 2019

(30) Foreign Application Priority Data

Sep. 25, 2017 (KR) .................. 10-2017-0123419

(51) Int. Cl.
*A61N 1/36* (2006.01)
*A61N 1/02* (2006.01)
(Continued)

(52) U.S. Cl.
CPC ......... *A61N 1/36003* (2013.01); *A61N 1/025* (2013.01); *A61N 1/36053* (2013.01);
(Continued)

(58) Field of Classification Search
CPC ............ A61N 1/025; A61N 1/36003; A61N 1/36135; A61N 1/36103; A61N 1/36053; A61N 1/36139; A61N 1/36507; A61N 1/36031; A61N 1/36034; A61N 1/36178; A61N 1/36189; A61B 5/296; A61B 5/24; A61B 5/4836
See application file for complete search history.

(56) References Cited

U.S. PATENT DOCUMENTS 8,380,317 B2   2/2013  Marineo
10,328,233 B2 *  6/2019  Tass ...................... A61M 21/00
(Continued)

FOREIGN PATENT DOCUMENTS

CN       102457252 A    5/2012
CN       104144728 A    11/2014
(Continued)

OTHER PUBLICATIONS

Wijekoon, Jayawan HB, and Piotr Dudek. "Compact silicon neuron circuit with spiking and bursting behaviour." Neural Networks 21.2-3 (2008): 524-534 (Year: 2008).*
(Continued)

*Primary Examiner* — Shirley X Jian
(74) *Attorney, Agent, or Firm* — NSIP Law

(57) ABSTRACT

A neuromimetic stimulating apparatus includes a feedback detector configured to detect a feedback signal from a target to be stimulated, a controller configured to analyze a waveform of the detected feedback signal and determine a parameter based on the analyzed waveform of the detected feedback signal, and a signal generator configured to generate a stimulus signal corresponding to the detected feedback signal based on the determined parameter.

25 Claims, 14 Drawing Sheets

(51) Int. Cl.
*A61N 1/365* (2006.01)
*A61B 5/00* (2006.01)
*A61B 5/24* (2021.01)
*A61B 5/296* (2021.01)

(52) U.S. Cl.
CPC ..... *A61N 1/36103* (2013.01); *A61N 1/36135* (2013.01); *A61N 1/36139* (2013.01); *A61N 1/36507* (2013.01); *A61B 5/24* (2021.01); *A61B 5/296* (2021.01); *A61B 5/4836* (2013.01); *A61N 1/36031* (2017.08); *A61N 1/36034* (2017.08); *A61N 1/36178* (2013.01); *A61N 1/36189* (2013.01)

(56) References Cited

U.S. PATENT DOCUMENTS

| | | | |
|---|---|---|---|
| 2001/0023362 A1* | 9/2001 | Kobayashi | A61N 1/36034 607/72 |
| 2004/0220621 A1* | 11/2004 | Zhou | A61N 1/36071 607/2 |
| 2004/0236391 A1* | 11/2004 | Kobayashi | A61N 1/025 607/72 |
| 2006/0155340 A1 | 7/2006 | Schuler et al. | |
| 2006/0224210 A1* | 10/2006 | Stellar | A61B 5/4519 607/46 |
| 2007/0299895 A1* | 12/2007 | Johnson | G06F 1/0321 708/270 |
| 2010/0286748 A1* | 11/2010 | Midani | A61N 1/36003 607/48 |
| 2011/0137371 A1* | 6/2011 | Giftakis | A61B 5/4094 607/45 |
| 2012/0029591 A1* | 2/2012 | Simon | A61N 1/40 607/42 |
| 2012/0239108 A1 | 9/2012 | Foutz et al. | |
| 2012/0259382 A1* | 10/2012 | Trier | A61N 1/36071 607/46 |
| 2013/0204319 A1* | 8/2013 | Trier | A61N 1/36146 607/46 |
| 2013/0310909 A1* | 11/2013 | Simon | A61N 1/36025 607/115 |
| 2014/0100628 A1 | 4/2014 | Pu et al. | |
| 2014/0257438 A1* | 9/2014 | Simon | A61N 2/02 607/150 |
| 2015/0018706 A1 | 1/2015 | Segal | |
| 2015/0039051 A1* | 2/2015 | Popovic | A61N 1/0476 607/48 |
| 2015/0080987 A1 | 3/2015 | Deere et al. | |
| 2016/0129248 A1 | 5/2016 | Creasey et al. | |
| 2016/0175589 A1 | 6/2016 | Wingeier | |
| 2016/0193465 A1 | 7/2016 | Knudson et al. | |
| 2016/0206880 A1 | 7/2016 | Koubeissi | |
| 2017/0056643 A1 | 3/2017 | Herb et al. | |
| 2017/0113048 A1 | 4/2017 | Giftakis et al. | |
| 2017/0172497 A1* | 6/2017 | Marquez Chin | G16H 20/30 |
| 2018/0117318 A1* | 5/2018 | Milekovic | A61B 5/0036 |
| 2018/0133471 A1 | 5/2018 | Lee et al. | |
| 2018/0296834 A1* | 10/2018 | John | A61N 1/36007 |
| 2020/0179697 A1* | 6/2020 | Schepis | A61N 1/36135 |

FOREIGN PATENT DOCUMENTS

| | | |
|---|---|---|
| CN | 104605853 A | 5/2015 |
| EP | 2004283 A1 | 12/2008 |
| JP | 8-507240 A | 8/1996 |
| JP | 2004-350859 A | 12/2004 |
| JP | 2008-543357 A | 12/2008 |
| JP | 2008-543429 A | 12/2008 |
| JP | 2013-523410 A | 6/2013 |
| KR | 10-2004-0068924 A | 8/2004 |
| WO | WO 2015/160964 A1 | 10/2015 |

OTHER PUBLICATIONS

Izhikevich, Eugene M., "Simple Model of Spiking Neurons", *IEEE Transactions on Neural Networks*, vol. 14, Issue 6, Nov. 2003 (pp. 1569-1572).

Wijekoon, Jayawan H B et al., "Simple Analogue VLSI Circuit of a Cortical Neuron", *2006 13th IEEE International Conference on Electronics, Circuits and Systems*, 2006, (pp. 1344-1347).

Wijekoon, Jayawan H.B., et al., "Compact silicon neuron circuit with spiking and bursting behaviour." *Neural Networks*, vol. 21, Issue 2-3, 2008 (pp. 524-534).

Grassia, Filippo, et al. "Tunable neuromimetic integrated system for emulating cortical neuron models." *Frontiers in Neuroscience*, vol. 5, Article 134, Dec. 7, 2011 (pp. 1-12).

Park, Hong Sik, et al., "Scrambler Therapy for Patients with Cancer Pain-Case Series." *The Korean Journal of Pain*, vol. 26, Issue 1, Jan. 2013 (pp. 65-71).

Lee, Dong-Kyu, et al., "Effect of pain scrambler therapy on shoulder joint pain and range of motion in patients who had undergone arthroscopic rotator cuff repair for the first time." *Journal of Physical Therapy Science*, vol. 28, Issue 7, Jul. 2016 (pp. 2175-2177).

Extended European Search Report dated Dec. 12, 2018, in counterpart European Application No. 18194314.3 (8 pages in English).

Korean Office Action dated Mar. 22, 2022, in counterpart Korean Patent Application No. 10-2017-0123419 (3 pages in English and 6 pages in Korean).

Japanese Office Action dated Oct. 25, 2022, in counterpart Japanese Patent Application No. 2018-177679 (5 Pages in Japanese, 3 Pages in English).

European Office Action dated Sep. 23, 2022, in counterpart European Patent Application No. 18 194 314.3 (6 pages in English).

* cited by examiner

400

NEUROMIMETIC STIMULATING APPARATUS AND METHOD

CROSS-REFERENCE TO RELATED APPLICATIONS

This application claims the benefit under 35 USC 119(a) of Korean Patent Application No. 10-2017-0123419 filed on Sep. 25, 2017, in the Korean Intellectual Property Office, the entire disclosure of which is incorporated herein by reference for all purposes.

BACKGROUND

1. Field

The following description relates to a neuromimetic stimulating apparatus and method.

2. Description of Related Art

A stimulating apparatus applies an electrical stimulation to a body part, for example, a brain, a heart, a stomach, or a muscle. When the electric stimulation is applied, a predetermined response occurs in the body part. Treatment, rehabilitation, and aesthetic procedures are performed using the response. Nerves in each body part generate predetermined neural signals based on a predetermined situation, and a predetermined physical function may be realized by the neural signals generated by the nerves. The stimulating apparatus influences the nerves or the neural signals through the electrical stimulation.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a stimulating apparatus includes a feedback detector configured to detect a feedback signal from a target to be stimulated; a controller configured to analyze a waveform of the detected feedback signal and determine a parameter based on the analyzed waveform of the detected feedback signal; and a signal generator configured to generate a stimulus signal corresponding to the detected feedback signal based on the determined parameter.

The controller may be further configured to determine a neural response indicated by the detected feedback signal based on the analyzed waveform of the detected feedback signal, and determine the parameter based on the determined neural response.

The controller may be further configured to determine the neural response indicated by the detected feedback signal by obtaining the neural response indicated by the detected feedback signal from a data set storing feedback signals and neural responses mapped to the feedback signals based on the analyzed waveform of the detected feedback signal.

The feedback signals stored in the data set may be obtained by exposing the target to environments that induce the neural responses stored in the data set.

The controller may be further configured to determine the parameter by obtaining a stimulus signal corresponding to the determined neural response from a data set storing neural responses and stimulus signals mapped to the neural responses, and determine the parameter based on the obtained stimulus signal.

The controller may be further configured to determine a category to which the detected feedback signal belongs among categories of neural signals, and analyze the waveform of the detected feedback signal by detecting an interval between peaks in the detected feedback signal.

The stimulus signal may be effective to induce in the target a physical function corresponding to the stimulus signal in response to the stimulus signal being applied to the target.

The stimulus signal may be configured to mimic a neural signal occurring in the target.

The signal generator may include an analog circuit configured to output an analog signal corresponding to a waveform of the stimulus signal based on the determined parameter.

The analog circuit may include capacitors and transistors, and may be further configured to output the analog signal in response to an input signal corresponding to the determined parameter being applied to any one or any combination of any two or more of the capacitors and the transistors.

The capacitors may include a first capacitor and a second capacitor, the first capacitor may be configured to generate a signal in a first frequency band in the analog signal based on the input signal, and the second capacitor may be configured to generate pulses having a frequency in a second frequency band on peaks of the signal in the first frequency based on the input signal.

The controller may be further configured to determine the parameter to be effective to induce a predetermined physical function in the target, and the signal generator may be further configured to generate the stimulus signal to be effective to induce the predetermined physical function in the target based on the determined parameter.

In another general aspect, a stimulating method includes detecting a feedback signal from a target to be stimulated; analyzing a waveform of the detected feedback signal; determining a parameter based on the analyzed waveform of the detected feedback signal; and generating a stimulus signal corresponding to the detected feedback signal based on the determined parameter.

The stimulating method may further include determining a neural response indicated by the detected feedback signal based on the analyzed waveform of the detected feedback signal, and the determining of the parameter may include determining the parameter based on the determined neural response.

The determining of the neural response indicated by the detected feedback signal may include obtaining the neural response indicated by the detected feedback signal from a data set storing feedback signals and neural responses mapped to the feedback signals based on the analyzed waveform of the detected feedback signal.

The determining of the parameter may further include determining the parameter by obtaining a stimulus signal corresponding to the determined neural response from a data set storing neural responses and stimulus signals mapped to the neural responses; and determining the parameter based on the obtained stimulus signal.

The analyzing of the waveform of the detected feedback signal may include determining a category to which the detected feedback signal belongs among categories of neural signals; and detecting an interval between peaks in the detected feedback signal.

The generating of the stimulus signal may include inputting an input signal corresponding to the determined parameter into an analog circuit configured to output an analog signal corresponding to a waveform of the stimulus signal in response to the input signal.

The determining of the parameter may include determining the parameter to be effective to induce a predetermined physical function in the target, and the generating of the stimulus signal may include generating the stimulus signal to be effective to induce the predetermined physical function in the target based on the determined parameter.

In another general aspect, a non-transitory computer-readable medium stores instructions that, when executed by a processor, cause the processor to perform the stimulating method of claim described above.

In another general aspect, a stimulating apparatus includes a feedback detector configured to detect a feedback signal from a target to be stimulated; a memory configured to store instructions; a processor configured to execute the instructions stored in the memory to configure the processor to analyze the detected feedback signal to determine a stimulus signal to be applied to the target, and determine a parameter to be used to generate the stimulus signal; and a signal generator configured to generate the stimulus signal based on the parameter.

The processor may be further configured to analyze the detected feedback signal to determine a neural response indicated by the detected feedback signal, and determine, as the stimulus signal, a stimulus signal effective to induce in the target a physical function corresponding to the neural response in response to the stimulus signal being applied to the target.

The processor may be further configured to determine the neural response and the stimulus signal by referring to a data set storing feedback signals and corresponding neural responses, physical functions, and stimulus signals mapped to the feedback signals.

The processor may be further configured to determine a first parameter related to a waveform of the stimulus signal, and a second parameter related to a level of the stimulus signal, and the signal generator may be further configured to generate the stimulus signal based on the first parameter and the second parameter.

The processor may be further configured to analyze a waveform of the detected feedback signal to determine a neural response indicated by the detected feedback signal, in response to the neural response indicating a need to change a hormone level in the target, determine, as the stimulus signal, a first stimulus signal having a waveform different from the waveform of the detected feedback signal, the waveform of the first stimulus signal being effective to change the hormone level in the target in response to the first stimulus signal being applied to the target, and in response to the neural response indicating a motor nerve is to be actuated in the target, determine, as the stimulus signal, a second stimulus signal having a waveform substantially the same as the waveform of the detected feedback signal, the waveform of the second signal being effecting to activate the motor nerve in the target in response to the second stimulus signal being applied to the target.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
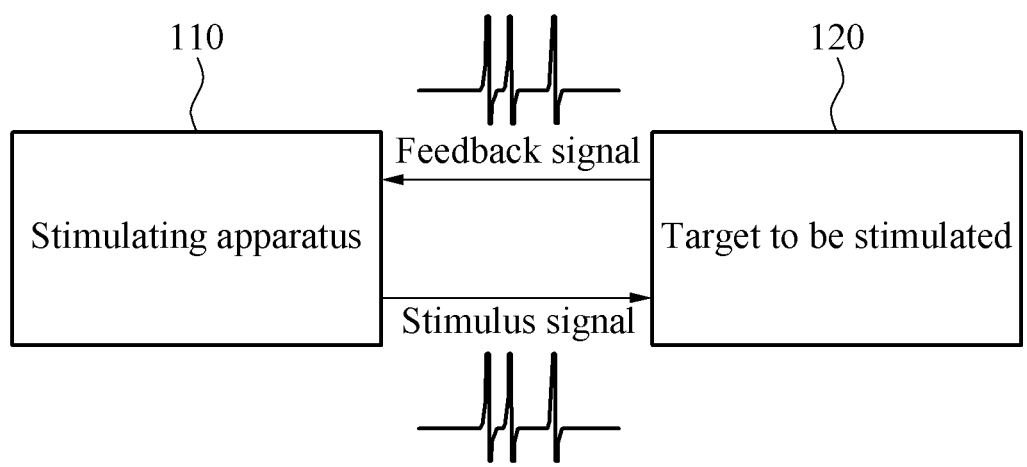
FIG. 1 illustrates an example of a neuromimetic stimulating system.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, components, and/or combinations thereof, but do not preclude the presence or addition of one or more other features, numbers, operations, members, elements, components, and/or combinations thereof.

Unless otherwise defined, all terms, including technical and scientific terms, used herein have the same meaning as commonly understood by one of ordinary skill in the art to which the disclosure of this application pertains based on an understanding of the disclosure of this application. Terms, such as those defined in commonly used dictionaries, are to be interpreted as having a meaning that is consistent with their meaning in the context of the relevant art and the disclosure of this application, and are not to be interpreted in an idealized or overly formal sense unless expressly so defined herein.

FIG. 1 illustrates an example of a neuromimetic stimulating system. Referring to FIG. 1, a stimulating apparatus 110 detects a feedback signal from a target 120 to be stimulated, and applies a stimulus signal to the target 120 based on the detected feedback signal.

Examples of the target 120 include a body part such as a brain, a heart, a stomach, or a muscle, a cell in the body part, or a nerve in the body part, but the target 120 is not limited thereto. Furthermore, the target 120 corresponds to a unit of a cell, a tissue, or an organ. For example, the target 120 is any one of a brain cell, a brain tissue, and the brain itself. The target 120 uses neural signals to exchange information in a body, or to realize a physical function. The stimulating apparatus 110 detects a neural signal generated by the target 120 as the feedback signal, and applies the stimulus signal to the target 120 to act as the neural signal.

Detection of the feedback signal from the target 120 includes detection of a feedback signal in a periphery of the target 120 to detect the feedback signal from the target 120. In one example, the stimulating apparatus 110 detects a feedback signal in a periphery of a vagus nerve to detect a feedback signal from the vagus nerve. Application of the stimulus signal to the target 120 includes application of a stimulus signal to a periphery of the target 120 to apply the stimulus signal to the target 120. In one example, the stimulating apparatus 110 applies a stimulus signal to a periphery of a stomach tissue to apply the stimulus signal to the stomach tissue.

The stimulating apparatus 110 stimulates the target 120 for treatment, rehabilitation, and aesthetic purposes. For example, the stimulating apparatus 110 is used as a medical device, for example, a deep brain stimulator, a pacemaker, an electrical muscle stimulator, a physical therapy device, or an electric needle. The electrical muscle stimulator and the electric needle may be used for a medical purpose, a health care purpose such as relaxation of muscles, or an aesthetic purpose such as growth of muscles, correction of muscle shapes, or lipolysis. Such a medical device is attached to a body or inserted into the body to apply a stimulus signal to the body. In another example, the stimulating apparatus 110 is also used for a cosmetic purpose such as skin care or scar repair.

The target 120 generates a neural signal having a predetermined meaning when the target is exposed to a predetermined environment. For example, in a case in which food is ingested, the target 120 generates a neural signal to secrete a digestive fluid. A response appearing as a neural signal when the target 120 is exposed to a predetermined environment is referred to as a neural response. Different neural responses are generated when the target 120 is exposed to different environments. A neural signal having a predetermined waveform is generated based on a neural response. The stimulating apparatus 110 determines a neural response corresponding to the feedback signal by analyzing a waveform of the feedback signal.

The stimulating apparatus 110 extracts a feature point from the feedback signal, and analyzes the waveform of the feedback signal based on the extracted feature point. The stimulating apparatus 110 extracts the feature point from the feedback signal to reflect a feature of the waveform of the feedback signal. In one example, the neural signal is classified based on an interval between peaks in the neural signal. The stimulating apparatus 110 analyzes the waveform of the feedback signal by extracting the feature point from the peaks of the feedback signal. In another example, the stimulating apparatus 110 extracts the feature point at a predetermined sampling rate such that the entire waveform of the feedback signal is represented by the extracted feature points.

The neural signal is classified as one of predetermined categories of neural signals based on the waveform of the feedback signal. For example, the neural signal is classified as a tonic type signal, an adapting type signal, a transient type signal, a chattering type signal, a bursting type signal, a low threshold type signal, a regular type signal, a fast type signal, or a resonator type signal. These categories are merely an example of the predetermined categories, and the predetermined categories may include other types of neural signals. The stimulating apparatus 110 determines a category to which the feedback signal belongs among the plurality of categories, and analyzes the waveform of the feedback signal based on the determined category.

In addition, the waveform of the feedback signal is analyzed based on a signal level, a duration, a number of peaks, a number of clusters, a resonation, or a bursting. The stimulating apparatus 110 interprets the neural response corresponding to the feedback signal by analyzing the waveform of the feedback signal.

The stimulating apparatus 110 uses a pre-constructed data set to interpret a neural response occurring in the target 120 through the feedback signal. The data set stores feedback signals and neural responses mapped to the feedback signals. The data set is constructed by mapping, to a predetermined neural response, a feedback signal obtained when exposing the target 120 to an environment that induces the predetermined neural response. For example, a feedback signal obtained when the target 120 ingests food is mapped to a neural response of digestive fluid secretion. The stimulating apparatus 110 determines a neural response corresponding to the feedback signal detected from the target 120 by referring to the data set. In the above example, the stimulating apparatus 110 analyzes the feedback signal generated by the target 120 through the data set, and determines that the corresponding feedback signal induces digestive fluid secretion.

The stimulating apparatus 110 generates the stimulus signal based on a result of analyzing the feedback signal. For example, the stimulating apparatus 110 generates the stimulus signal to induce a physical function intended through the detected feedback signal in the target 120. The physical function intended through the detected feedback signal is a same function as the neural response triggering the detected feedback signal, or a function associated with the corresponding neural response. Thus, the stimulating apparatus 110 generates a stimulus signal having a waveform that is the same as the waveform of the feedback signal, or generates a stimulus signal having a waveform that is different from the waveform of the feedback signal. For example, in a case in which a feedback signal to induce a motor function is detected, the stimulating apparatus 110 generates a stimulus signal having a waveform that is the same as the waveform of the feedback signal. This operation is used to assist a cut motor nerve. In a case in which a feedback signal corresponding to food ingestion is detected as in the above example, the stimulating apparatus 110 generates a stimulus signal for insulin secretion. The waveform of the feedback signal corresponding to food ingestion is different from a waveform of the stimulus signal for insulin secretion.

The stimulating apparatus 110 generates the stimulus signal using the pre-constructed data set. The data set stores a stimulus signal mapped to each neural response. For example, the data set stores a stimulus signal to activate a motor nerve by mapping the stimulus signal to a motor nerve activation response, and stores a stimulus signal for insulin secretion by mapping the stimulus signal to a food ingestion response. When the neural response corresponding to the feedback signal is determined to be the motor nerve activation response, the stimulating apparatus 110 generates the stimulus signal to activate the motor nerve by referring to the data set. When the neural response corresponding to the feedback signal is determined to be the food ingestion response, the stimulating apparatus 110 generates the stimulus signal for insulin secretion by referring to the data set.

To activate the intended physical function in the target 120, the stimulus signal needs to be generated in a form of a neural signal of the natural world. In a case of using a square wave as the stimulus signal, although a predetermined influence will be applied to the target 120, it may be difficult to activate the intended physical function in the target 120 using the square wave. For example, a feeling of hunger may be suppressed by interrupting a neural signal that triggers a feeling of hunger occurring in the target 120 by applying a square wave as the stimulus signal. However, it is difficult to activate a physical function such as glucagon secretion in the target 120 using a square wave as the stimulus signal.

A neural signal of the natural world exists in a form of an irregular analog signal including a number of peaks. The stimulating apparatus 110 activates the intended physical function in the target 120 by mimicking the neural signal of the natural world, that is, the neural signal occurring in the target 120. In one example, the stimulating apparatus 110 generates the stimulus signal using an analog circuit. The analog circuit is designed based on a mathematical model to mimic the neural signal of the natural world. The stimulating apparatus 110 applies a predetermined input signal to the analog circuit to generate a stimulus signal having a desired waveform, and the analog circuit generates the stimulus signal based on the applied input signal. The analog circuit does not operate at a high frequency or require a large memory, and thus operates using a low power and is implemented in a small size.

As described above, the stimulating apparatus 110 detects a feedback signal, and generates a stimulus signal corresponding to the detected feedback signal. In another example, the stimulating apparatus 110 generates a stimulus signal without detecting a feedback signal. For example, in a case requiring a predetermined stimulus signal for muscle recovery, the stimulating apparatus 110 continuously applies the stimulus signal to the target 120 irrespective of detection of a feedback signal. In this example, the stimulating apparatus 110 obtains a parameter to generate the stimulus signal from a pre-stored data set, and generates the stimulus signal based on the obtained parameter.

Figure 2:
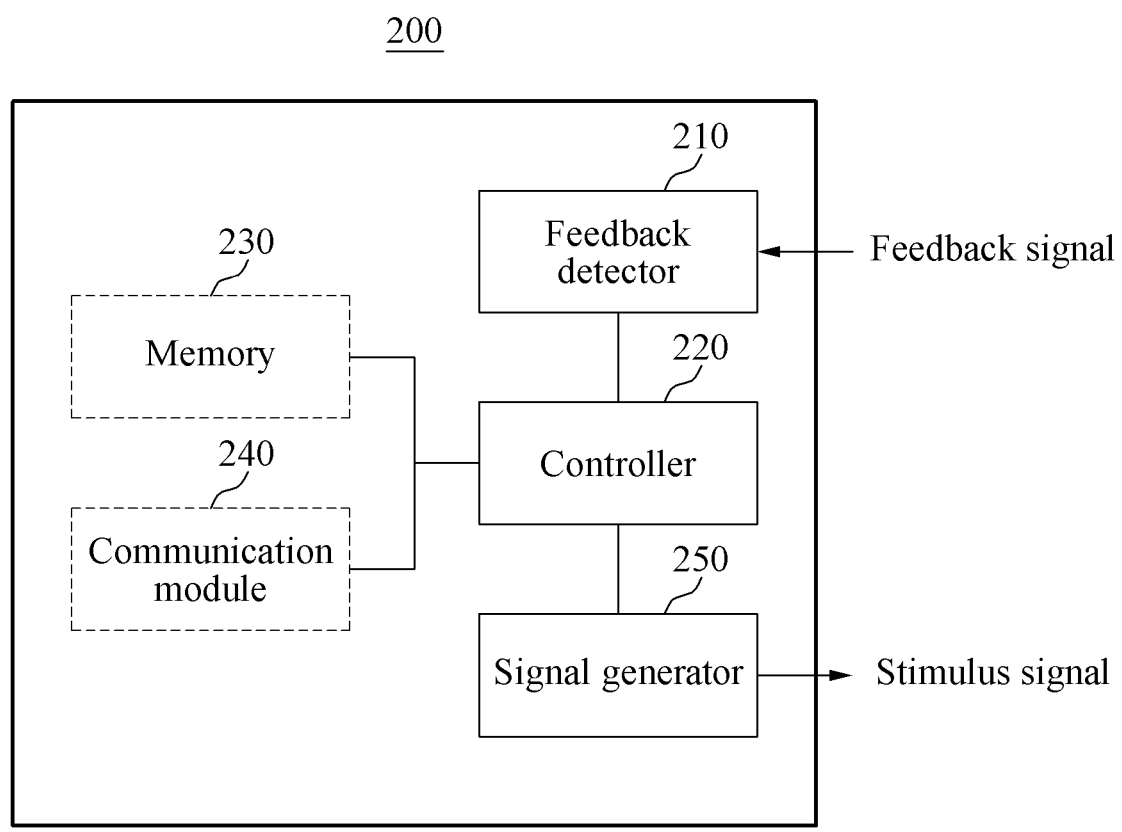
FIG. 2 is a block diagram illustrating an example of a stimulating apparatus.

FIG. 2 is a block diagram illustrating an example of a stimulating apparatus. Referring to FIG. 2, a stimulating apparatus 200 includes a feedback detector 210, a controller 220, and a signal generator 250. The stimulating apparatus 200 may also include either one or both of a memory 230 and a communication module 240.

The feedback detector 210 detects a neural signal occurring in a target to be stimulated as a feedback signal. A position at which the feedback signal is detected in the target is referred to as a measurement point. The measurement point is a position at which the neural signal occurs in the target, or a periphery of the position at which the neural signal occurs in the target. The measurement point may be spaced apart from a position to which a stimulus signal is applied. The feedback detector 210 detects the feedback signal from a skin of the target, an internal organ of the target, or an internal tissue of the target. The feedback detector 210 detects the feedback signal from the target through an electrode or a patch through which electricity flows.

The feedback detector 210 filters and amplifies the detected feedback signal, and transmits the processed feedback signal to the controller 220. For example, the feedback detector 210 filters high-frequency noise and low-frequency noise out of the detected feedback signal, and amplifies a medium frequency band of the feedback signal. The high-frequency noise includes white noise generated a vibration occurring during an operation of the stimulating apparatus 200, and the low-frequency noise includes noise generated by a movement of the stimulating apparatus 200 or an impact applied to the stimulating apparatus 200.

The controller 220 analyzes a waveform of the feedback signal, and determines a parameter to be used to generate a stimulus signal based on the analyzed waveform of the feedback signal. The controller 220 analyzes the waveform of the feedback signal by extracting feature points from the feedback signal, and uses a category of the feedback signal, an interval between peaks, a signal level, a duration, a number of peaks, a number of clusters, a resonation, or a bursting for the analysis.

The parameter is associated with a waveform of the stimulus signal. For example, a neural signal is classified as one of predetermined categories of neural signals based on its waveform. The parameter is determined so that the stimulus signal belongs to one of the categories. Furthermore, the parameter determines a level of the stimulus signal, a duration, a number of peaks, an interval between peaks, a number of clusters, a resonation, or a bursting.

The controller 220 includes a hardware module and/or a processor. The controller 220 executes instructions stored in the memory 230 or an internal memory (not shown) of the controller 220, or instructions received through the communication module 240, to perform the operations described in this application. The controller 220 determines the parameter by referring to a pre-constructed data set. The data set stores feedback signals, neural responses, and stimulus signals that are mapped to each other. The controller 220 identifies a neural response corresponding to the feedback signal detected by the feedback detector 210 by referring to the data set, and determines the parameter to generate the stimulus signal corresponding to the identified neural response.

The controller 220 obtains the data set from the memory 230 and/or the communication module 240. In one example, the memory 230 stores the pre-constructed data set, and the controller 220 accesses the data set stored in the memory 230. In another example, the data set is stored in an external device, and the controller 220 accesses the data set stored in the external device through the communication module 240.

The signal generator 250 generates the stimulus signal corresponding to the feedback signal based on the determined parameter. For example, the controller 220 applies an input signal corresponding to the determined parameter to the signal generator 250, and the signal generator 250 generates the stimulus signal based on the applied input signal. The signal generator 250 includes an analog circuit and a driver circuit. The analog circuit outputs an analog signal corresponding to a waveform of the stimulus signal based on the input signal, and the driver circuit outputs the stimulus signal by adjusting a level of the analog signal based on the input signal.

Figure 3:
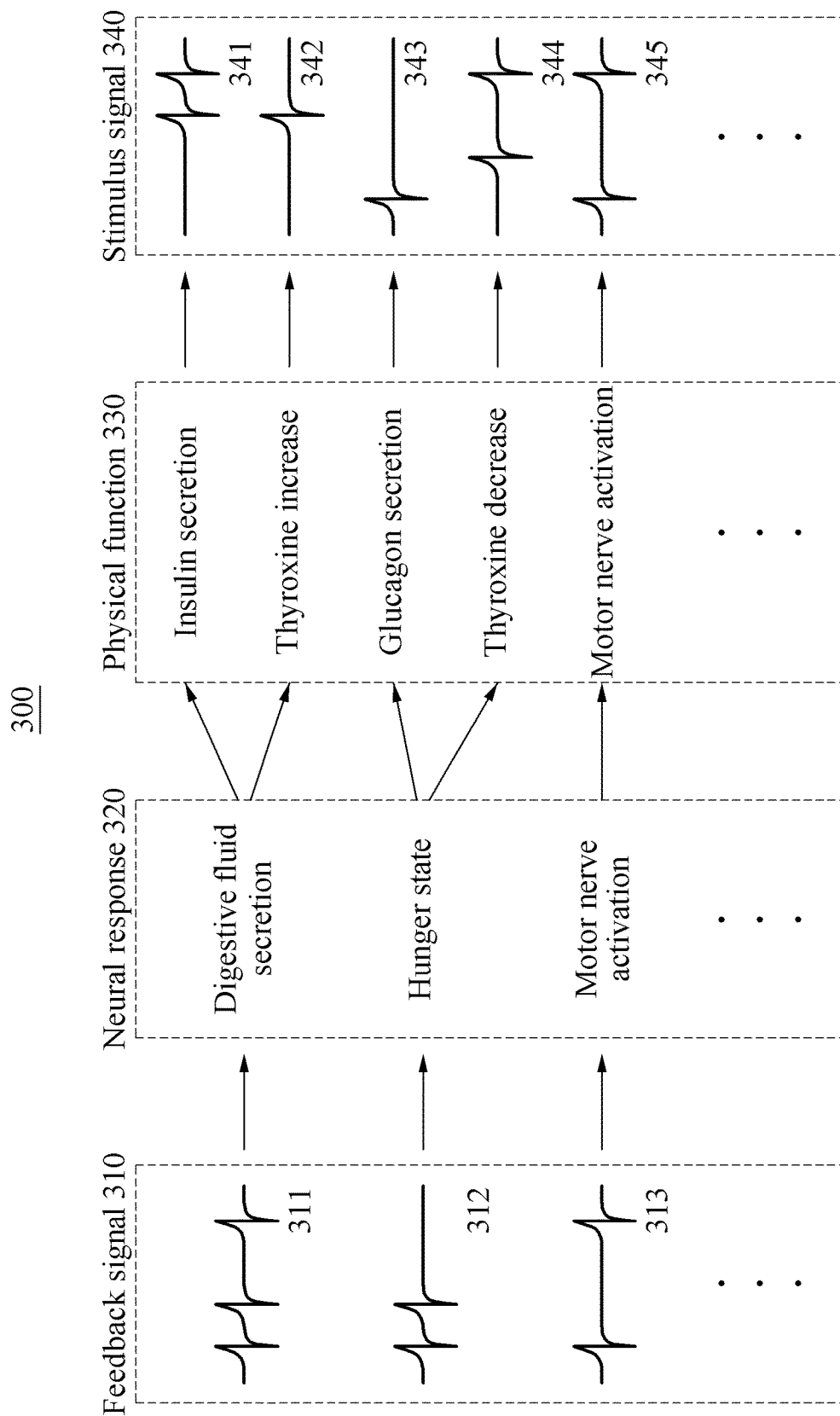
FIG. 3 illustrates an example of a data set.

FIG. 3 illustrates an example of a data set. Referring to FIG. 3, a data set 300 stores information related to a feedback signal 310, a neural response 320, a physical function 330, and a stimulus signal 340. As one example, FIG. 3 illustrates feedback signals 311 through 313, neural responses of "digestive fluid secretion", "hunger state", and "motor nerve activation", and physical functions of "insulin secretion", "thyroxine increase", "glucagon secretion", and "thyroxine decrease", and "motor nerve activation", and stimulus signals 341 through 345. However, the feedback signal 310, the neural response 320, the physical function 330, and the stimulus signal are not limited to the examples in FIG. 3, and the data set 300 may include various other feedback signals 310, neural responses 320, physical functions 330, and stimulus signals 340. The data set 300 is stored in a memory of a stimulating apparatus or an external device. The stimulating apparatus obtains the data set 300 from the memory of the stimulating apparatus, or obtains the data set 300 by accessing the external device through a communication module of the stimulating apparatus.

The data set 300 stores mapping information between the feedback signal 310 and the neural response 320. For example, the feedback signal 311 is mapped to the neural response of "digestive fluid secretion", the feedback signal 312 is mapped to the neural response of "hunger state", and the feedback signal 313 is mapped to the neural response of "motor nerve activation". The stimulating apparatus determines a neural response corresponding to a feedback signal detected from a target to be stimulated by referring to the mapping information.

A waveform of the feedback signal 310 and the mapping information between the feedback signal 310 and the neural response 320 are determined experimentally. For example, the feedback signal 310 obtained by exposing the target to an environment that induces the neural response 320 is mapped to the neural response 320 in the data set 300. The feedback signal 311 obtained in a state of food ingestion is mapped to the neural response of "digestive fluid secretion", and the feedback signal 312 obtained in a hunger state is mapped to the neural response of "hunger state".

The data set 300 also stores mapping information between the neural response 320 and the physical function 330. A predetermined function to be induced in the target based on the neural response 320 is stored as the physical function 330. For example, in a case in which a first physical function is to be induced based on a first neural response corresponding to a first feedback signal, the first neural response is mapped to the first physical function in the data set 300. When the first feedback signal is detected from the target, the stimulating apparatus generates a first stimulus signal to induce the first physical function in the target.

A single neural response is mapped to one or more physical functions. For example, the neural response of "digestive fluid secretion" is mapped to the physical function of "insulin secretion" and the physical function of "thyroxine increase", and the neural response of "hunger state" is mapped to the physical function of "glucagon secretion" and the physical function of "thyroxine decrease". Furthermore, in a case in which a stimulus signal having a waveform that is the same as the waveform of the detected feedback signal is to be provided, the neural response 320 and the physical function 330 are mapped as the same type signal. For example, the neural response of "motor nerve activation" is mapped to the physical function of "motor nerve activation". The same type signals of "motor nerve activation" may be used to assist a cut motor nerve.

The data set 300 also stores mapping information between the physical function 330 and the stimulus signal 340. The stimulus signal 340 is obtained in advance from the target in a situation in which the physical function 330 is induced in the target. For example, the stimulus signal 341 is obtained in a situation in which insulin is secreted in the target, and the stimulus signal 342 is obtained in a situation in which thyroxine is increased in the target. Similarly, the stimulus signal 343 is obtained in a situation in which glucagon is secreted in the target, the stimulus signal 344 is obtained in a situation in which thyroxine is decreased in the target, and the stimulus signal 345 is obtained in a situation in which motor nerve activation is induced in the target.

Thus, when a predetermined feedback signal is detected from the target, the stimulating apparatus generates a stimulus signal corresponding to the detected feedback signal by referring to the data set 300. Furthermore, in response to application of the generated stimulus signal to the target, a physical function corresponding to the stimulus signal is induced in the target.

Figure 4:
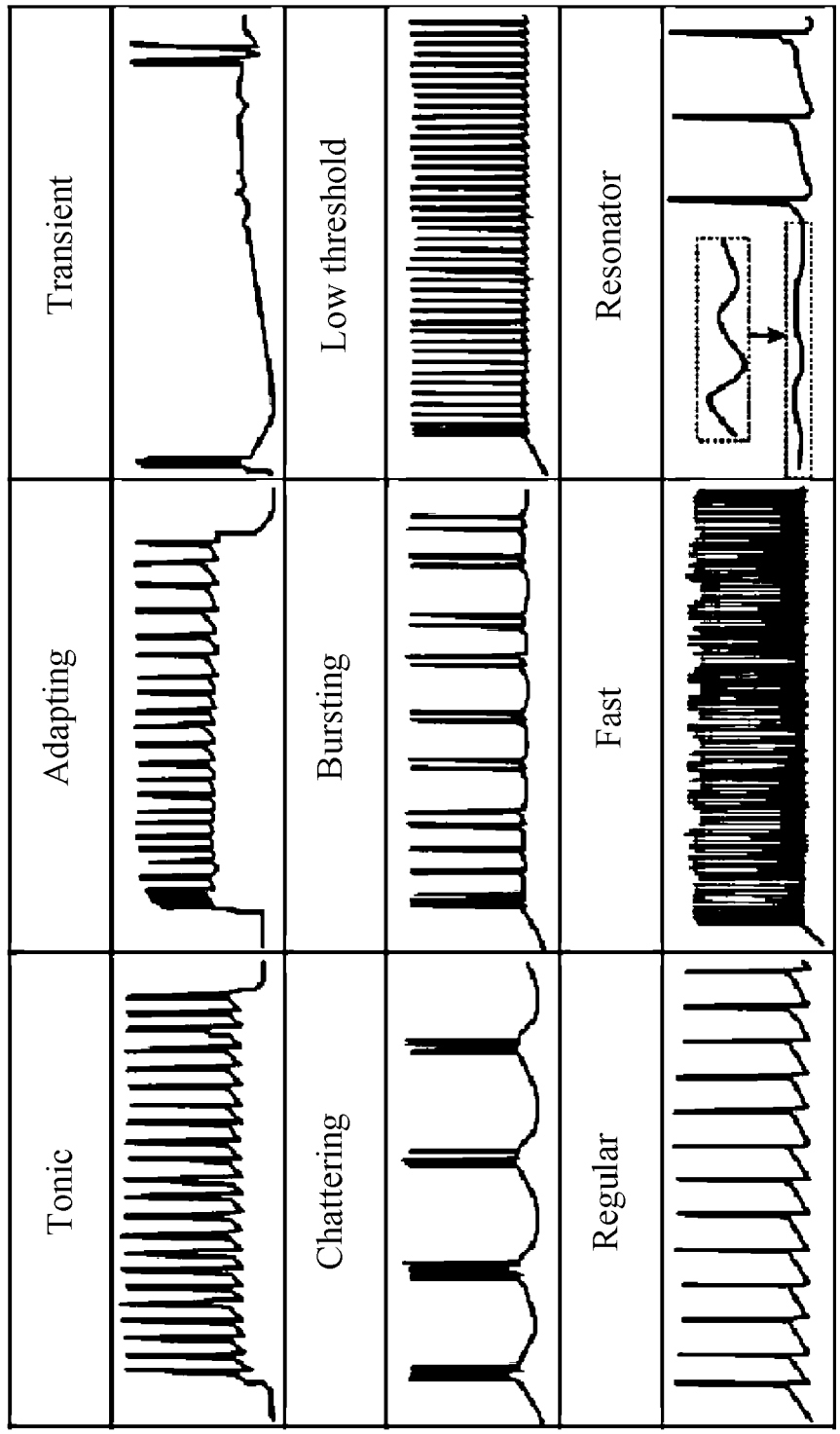
FIG. 4 illustrates an example of categories of neural signals.

FIG. 4 illustrates an example of categories of neural signals. Referring to FIG. 4, categories 400 of neural signals include a tonic type, an adapting type, a transient type, a chattering type, a bursting type, a low threshold type, a regular type, a fast type, and a resonator type. However, the categories 400 illustrated in FIG. 4 are merely an example, and the categories 400 are not limited thereto.

A tonic type signal exhibits peaks at a regular interval. An adapting type signal exhibits peaks at an interval that starts out small and gradually increases. A transient type signal exhibits sparse peaks at an irregular interval. A chattering type signal exhibits clusters of peaks, the clusters being spaced at a regular interval.

A bursting type signal includes a bursting section in which peaks are concentrated in comparison to other sections. A low threshold type signal includes relatively fine peaks. A regular type signal includes peaks at a regular interval, and includes a fewer number of peaks than the tonic type signal. A fast type signal includes exceedingly fine peaks, and includes a greater number of peaks than the low threshold type signal. A resonator type signal includes a resonator section including a temporary wave before peaks appear.

The stimulating apparatus analyzes a feedback signal by referring to the categories 400. For example, the stimulating apparatus determines a category to which the feedback signal belongs among the categories 400, determines a feature of the feedback signal, and analyzes the waveform of the feedback signal based on the determined feature.

Examples of a feature of the feedback signal include an interval between peaks, a signal level, a duration, a number of peaks, and a number of clusters, but the feature is not limited thereto. Furthermore, the stimulating apparatus generates a stimulus signal by referring to the categories 400. For example, the stimulating apparatus generates the stimulus signal by determining a category to which the stimulus signal belongs among the categories 400, and determines a feature of the stimulus signal.

Figure 5:
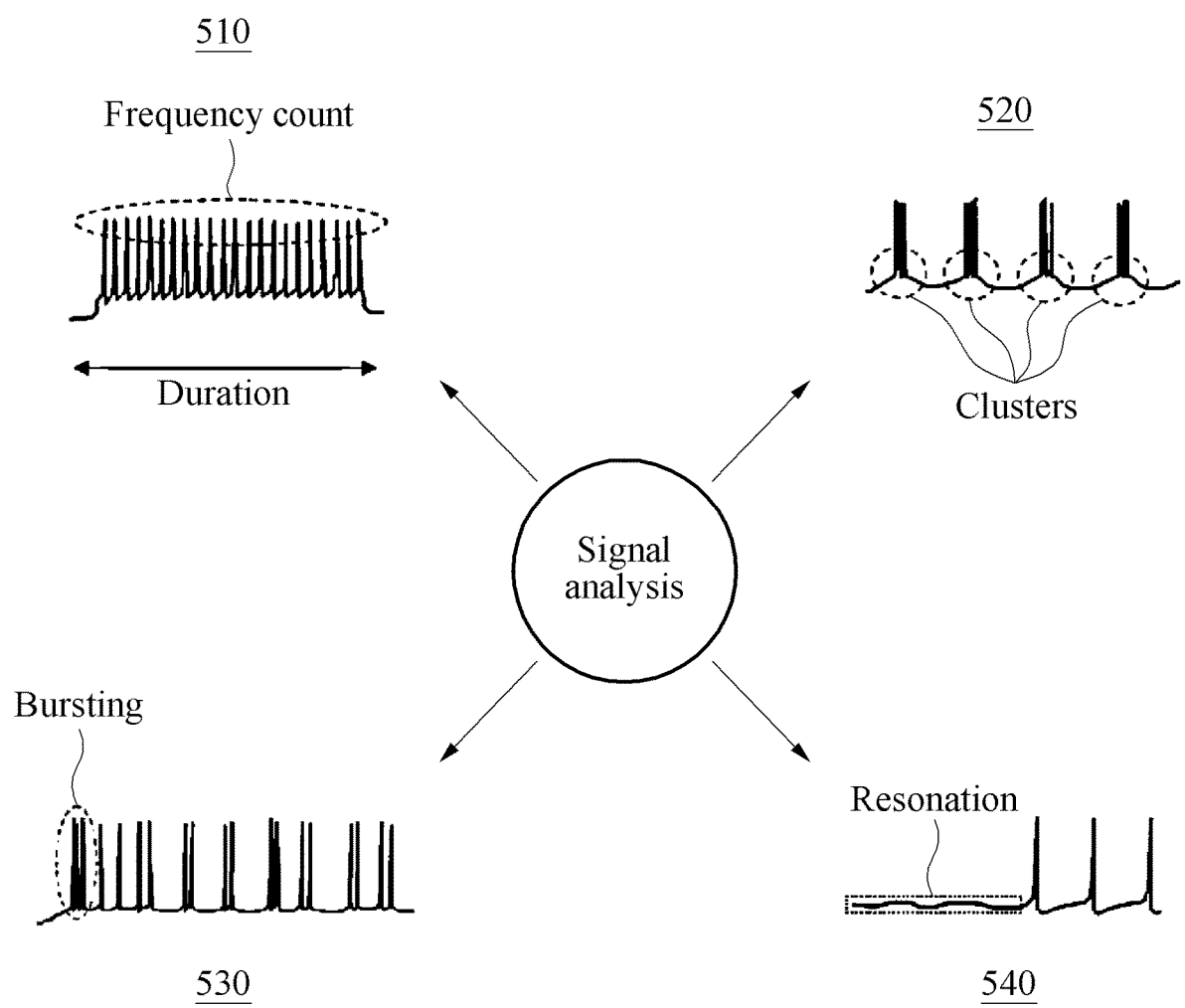
FIG. 5 illustrates an example of criteria for analyzing a neural signal.

FIG. 5 illustrates an example of criteria for analyzing a neural signal. Referring to FIG. 5, a stimulating apparatus analyzes a neural signal based on various criteria. A neural signal has a regular pattern. Neural signals 510 through 540 each show a single cycle of a regular pattern. Furthermore, criteria for analyzing the neural signals 510 through 540 are used to analyze a feedback signal or to generate a stimulus signal. The criteria for analyzing a neural signal illustrated in FIG. 5 are merely an example, and the criteria are not limited thereto.

In one example, the stimulating apparatus determines a frequency count of peaks and a duration in the neural signal 510. The duration is a duration of a single cycle of the neural signal 510. In another example, the stimulating apparatus analyzes an interval between the peaks and a frequency at which the peaks appear, instead of the frequency count of the peaks or in addition to the frequency count of the peaks. The interval between the peaks in the neural signal 510 is a constant interval. Thus, the neural signal 510 is classified as a tonic type signal or a regular type signal. Whether the neural signal 510 is a tonic type signal or a regular type signal is determined based on the frequency count of the peaks included in the neural signal 510.

The stimulating apparatus determines a presence of clusters, an interval between the clusters, and a number of the clusters in the neural signal 520. The neural signal 520 includes a number of clusters, and an interval between the clusters is a constant interval. Thus, the neural signal 520 is classified as a chattering type signal. The stimulating apparatus detects a bursting section in the neural signal 530, and classifies the neural signal 530 as a bursting type signal. The stimulating apparatus detects a resonator section in the neural signal 540, and classifies the neural signal 540 as a resonator type signal.

Similarly to the neural signal 510, the stimulating apparatus analyzes each of the neural signals 520, 530, and 540 by detecting a frequency count of peaks, an interval between the peaks, a frequency at which the peaks appear, and a duration in each of the neural signals 520, 530, and 540.

Figure 6:
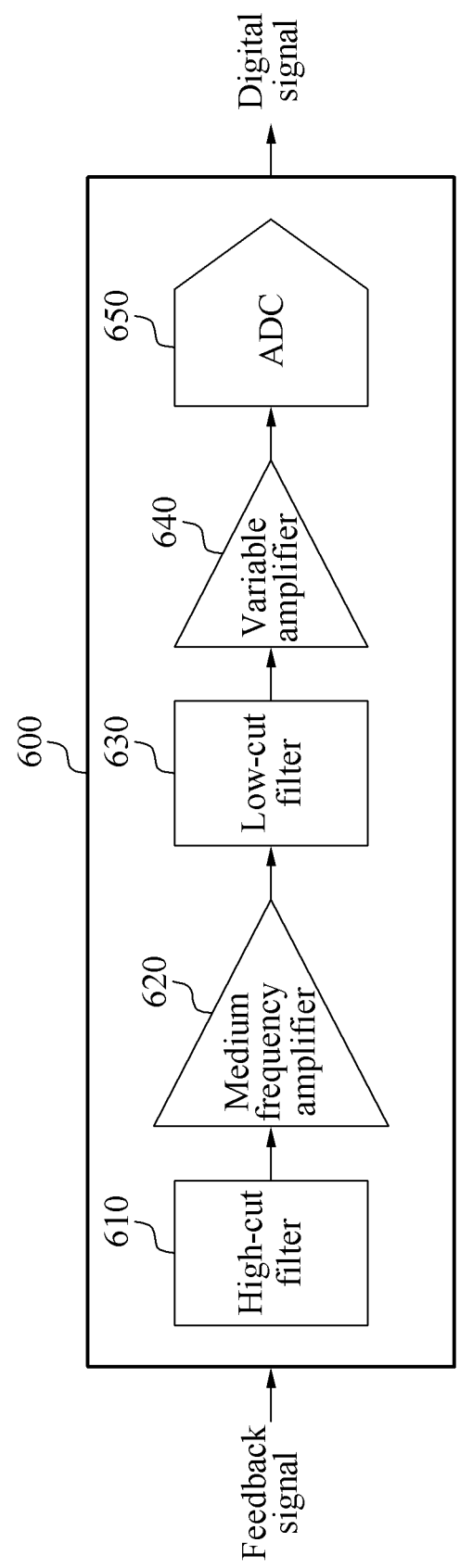
FIG. 6 is a block diagram illustrating an example of a feedback detector.

FIG. 6 is a block diagram illustrating an example of a feedback detector. Referring to FIG. 6, a feedback detector 600 includes a high-cut filter 610, a medium frequency amplifier 620, a low-cut filter 630, a variable amplifier 640, and an analog-to-digital converter (ADC) 650.

The high-cut filter 610 blocks high-frequency noise in a feedback signal. The high-frequency noise includes white noise generated by a vibration occurring during an operation of a stimulating apparatus. The medium frequency amplifier 620 amplifies a signal level of a medium frequency band in an output signal of the high-cut filter 610. The medium frequency band is predetermined based on a frequency of a neural signal. The low-cut filter 630 blocks low-frequency noise in an output signal of the medium frequency amplifier 620. The low-frequency noise includes noise generated by a movement of the stimulating apparatus or an impact applied to the stimulating apparatus. The variable amplifier 640 amplifies an output signal of the low-cut filter 630 to a level suitable for analyzing the feedback signal. The ADC 650 converts an output signal of the variable amplifier 640 into a digital signal and outputs the digital signal.

Figure 7:
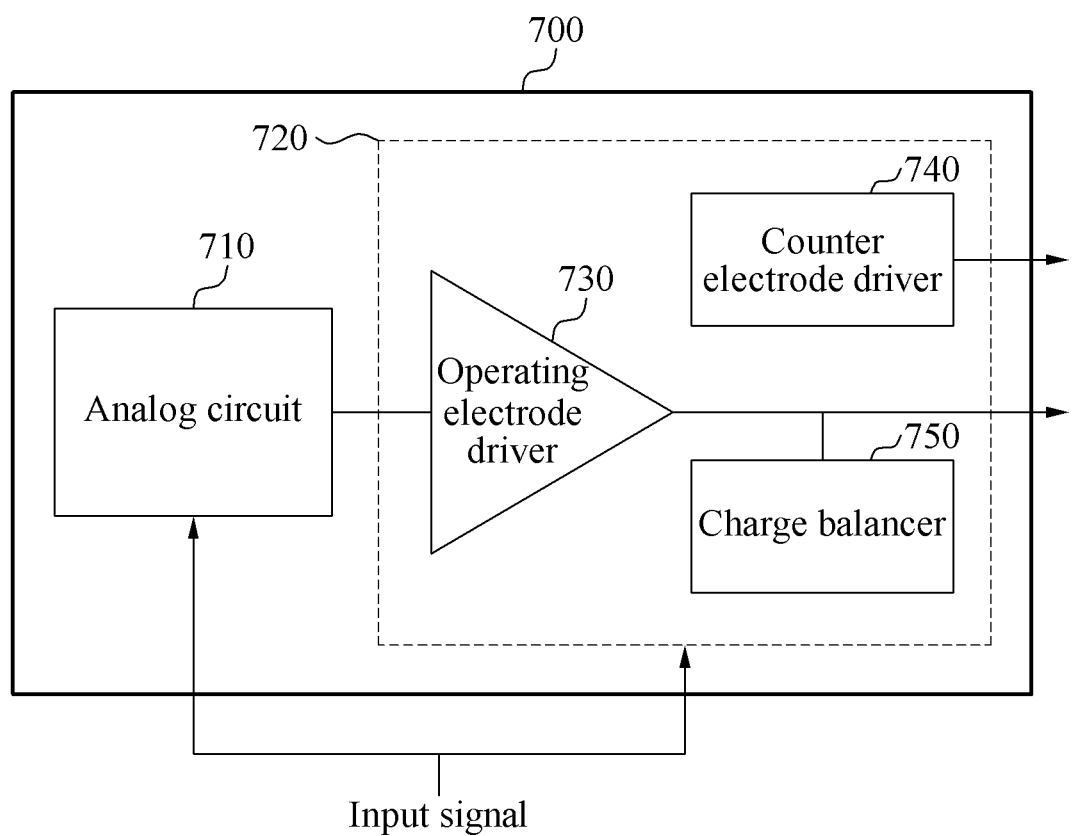
FIG. 7 is a block diagram illustrating an example of a signal generator.

FIG. 7 is a block diagram illustrating an example of a signal generator. Referring to FIG. 7, a signal generator 700 includes an analog circuit 710 and a driver circuit 720.

As described above, a controller of a stimulating apparatus analyzes a waveform of a feedback signal, and determines a parameter based on the waveform of the feedback signal. The parameter is determined for use in generating a stimulus signal corresponding to the feedback signal, and includes a first parameter related to a waveform of the stimulus signal and a second parameter related to a level of the stimulus signal. The controller transmits an input signal to the analog circuit 710 and the driver circuit 720 based on the determined parameters. The input signal includes a first input signal corresponding to the first parameter and a second input signal corresponding to the second parameter.

The analog circuit 710 outputs an analog signal corresponding to the waveform of the stimulus signal based on the first input signal. The analog circuit 710 is designed based on a mathematical model to mimic a neural signal of the natural world, and includes various analog devices that include capacitors and transistors. For example, the analog circuit 710 is designed based on a mathematical model such as a Hodgkin-Huxley model, an Izhikevich model, a Wilson model, a FitzHugh-Nagumo model, or a leaky integrate-and-fire (LIF) model. The analog circuit 710 outputs the analog signal in response to the input signal corresponding to the parameters determined by the controller being applied to any one or any combination any two or more of the capacitors and the transistors.

The analog circuit 710 does not operate at a high frequency or require a large memory, and thus operates using a low power and is implemented in a small size in comparison to a digital circuit. When the analog circuit 710 is used, a device such as an electronic medicine device requiring a long-term operation and a small size is implemented.

The driver circuit 720 adjusts a level of the analog signal based on the second input signal. The driver circuit 720 includes an operating electrode driver 730, a counter electrode driver 740, and a charge balancer 750. The operating electrode driver 730 and the counter electrode driver 740 receive an operating voltage, and output a stimulus signal by adjusting the level of the analog signal based on the second input signal. The charge balancer 750 supplies or outputs an electric charge to be used to generate the stimulus signal.

The operating electrode driver 730 injects a current to a target to be stimulated or extracts a current from the target. The strength of the stimulation with respect to time may be adjusted through the operating electrode driver 730.

The counter electrode driver 740 receives electric charges from the target when the operating electrode driver 730 injects a current to the target, and supplies electric charges to the target when the operating electrode driver 730 extracts a current from the target. The operating electrode driver 730 and the counter electrode driver 740 form a closed current circuit. Further, the counter electrode driver 740 may maintain a voltage at a level enabling a desired amount of current to be used for stimulation.

The charge balancer 750 blocks a direct current that may be generated as a potential of the target unintentionally increases or decreases. In an ideal case, an amount of injected current and an amount of extracted current for stimulation are equal to each other. In such a case, microscopically, the quantity of electric charges in the target does not change, and thus a direct current cannot be generated. However, if the quantity of electric charges of the target is skewed in a positive or negative direction due to an imbalance between the amount of the injected current and the amount of the extracted current, an undesired direct current may be generated and injure tissue of the target. To prevent this, the charge balancer 750 adjusts a level of the injected current or the extracted current if the potential of the target exceeds a reference potential after a predetermined time has elapsed.

Figure 8:
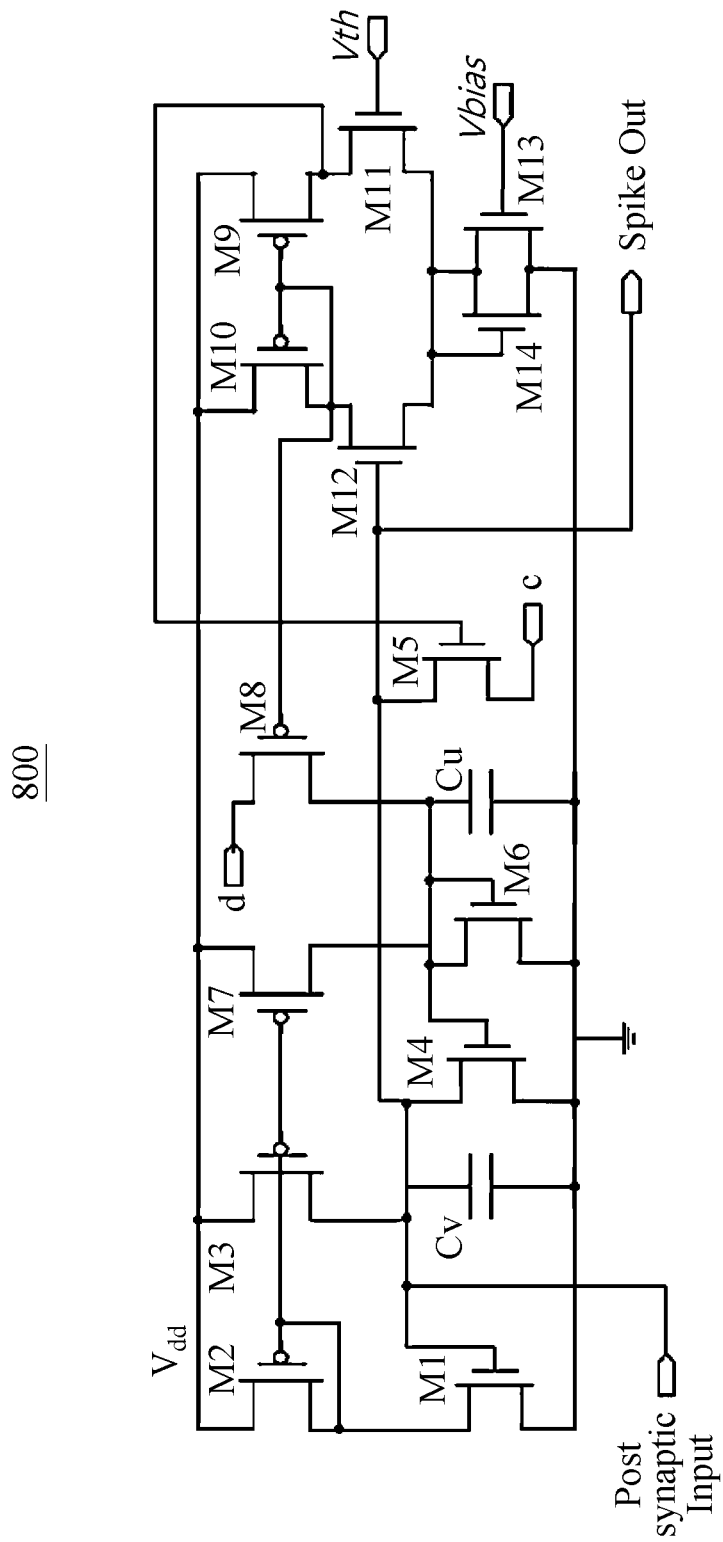
FIG. 8 is a circuit diagram illustrating an example of an analog circuit.

FIG. 8 is a circuit diagram illustrating an example of an analog circuit. As described above, various mathematical models may be used to mimic a neural signal of the natural world. Hereinafter, an analog circuit 800 based on an Izhikevich model will be described. However, a stimulus signal may be generated using another analog circuit based on the Izhikevich model, or another analog circuit based on another mathematical model.

Equation 1 below is obtained from the Izhikevich model.

$$v' = 0.04v^2 + 5v + 140 - u + I \qquad (1)$$
$$u' = a(bv - u)$$
$$\text{if } v \geq 30 \text{ mV, then } \begin{cases} v \leftarrow c \\ u \leftarrow u + d \end{cases}$$

In Equation 1, v denotes a membrane potential, v' denotes dv/dt, u denotes a membrane potential recovery variable, u' denotes du/dt, I denotes a post synaptic input current, a, b, c, and d denote parameters, and 30 mV denotes a threshold value. Constants in Equation 1 including the threshold value of 30 mV are determined experimentally. According to Equation 1, if the membrane potential v is greater than or equal to the threshold value of 30 mV, the membrane potential v is reset to be equal to the parameter c, and the membrane potential recovery variable u is reset to be equal to a sum of the membrane potential recovery variable u and the parameter d. Thus, the membrane potential v and the membrane potential recovery variable u are determined based on the parameters a, b, c, and d.

The analog circuit 800 is designed based on Equation 1. Referring to FIG. 8, the analog circuit 800 includes capacitors Cv and Cu, and transistors M1 through M14. The analog circuit 800 generates an output signal Spike Out based on the input signals c, d, and Post Synaptic Input, a threshold signal Vth, and a bias signal Vbias. The output signal Spike Out corresponds to the analog signal described above. The input signals c and d correspond to the parameters c and d of Equation 1, the input signal Post Synaptic Input corresponds to the post synaptic input current I of Equation 1, and the threshold signal Vth corresponds to the threshold value 30 mV of Equation 1. Device values of the capacitors Cv and Cu and the transistors M1 through M14 are determined based on the constants and the parameters a and b of Equation 1.

The capacitors Cv and Cu influence two elements of a waveform of the output signal Spike Out. In detail, the capacitor Cv influences the membrane potential, and the capacitor Cu influences the membrane potential recovery variable. In the analog circuit 800, the transistors M1 through M5 are parts related to the membrane potential, the transistors M1, M2, and M6 through M8 are parts related to the membrane potential recovery variable, and the transistors M9 through M14 are comparator parts. For ease of description, the parts related to the membrane potential recovery variable will be referred to as the recovery parts.

In the parts related to the membrane potential, a result of subtracting a leakage current provided by the transistor M4 from a sum of a current of the input signal Post Synaptic Input and a current provided by the transistor M3 is accumulated in the capacitor Cv, and the membrane potential is determined by the capacitor Cv. When the membrane potential reaches the input signal Vth, the comparator parts generate a first pulse that turns on the transistor M5 temporarily to reset the membrane potential to a voltage Vc. The voltage Vc corresponds to the input signal c.

A difference between a current provided by the transistor M7 and a current provided by the transistor M6 is accumulated in the capacitor Cu, and the membrane potential recovery variable is determined by the capacitor Cu. For ease of description, the membrane potential recovery variable will be referred to as a recovery variable. When the membrane potential reaches the threshold value, the comparator parts generate a second pulse that turns on the transistor M8 temporarily. When the transistor M8 is turned on, a surplus charge is accumulated in the capacitor Cu, which increases the recovery variable. An increase in the recovery variable is determined by the input signal d.

The threshold signal Vth and the bias signal Vbias respectively correspond to a threshold value and a bias voltage of the comparator parts. The bias signal Vbias controls a bias current in the comparator parts. When the membrane potential reaches a value of the threshold signal Vth, the comparator parts generate the first pulse and the second pulse, the first pulse resets the parts related to the membrane potential via the transistor M5 as discussed above, and the second pulse resets the recovery parts via the transistor M8 as discussed above.

The waveform of the output signal Spike Out is determined based on an increase and a decrease of the membrane potential, and an increase and a decrease of the recovery variable. The output signal Spike Out includes a wave of a first frequency band, and pulses of a second frequency band on peaks within the wave of the first frequency band. The first frequency band is lower than the second frequency band. The wave of the first frequency band is formed by the capacitor Cu based on the input signals c and d, and the pulses of the second frequency band are formed by the capacitor Cv based on the input signals c and d.

The waveform of the stimulus signal is determined based on the output signal Spike Out, and a signal generator generates the stimulus signal by appropriately adjusting a level of the output signal Spike Out.

Figure 9:
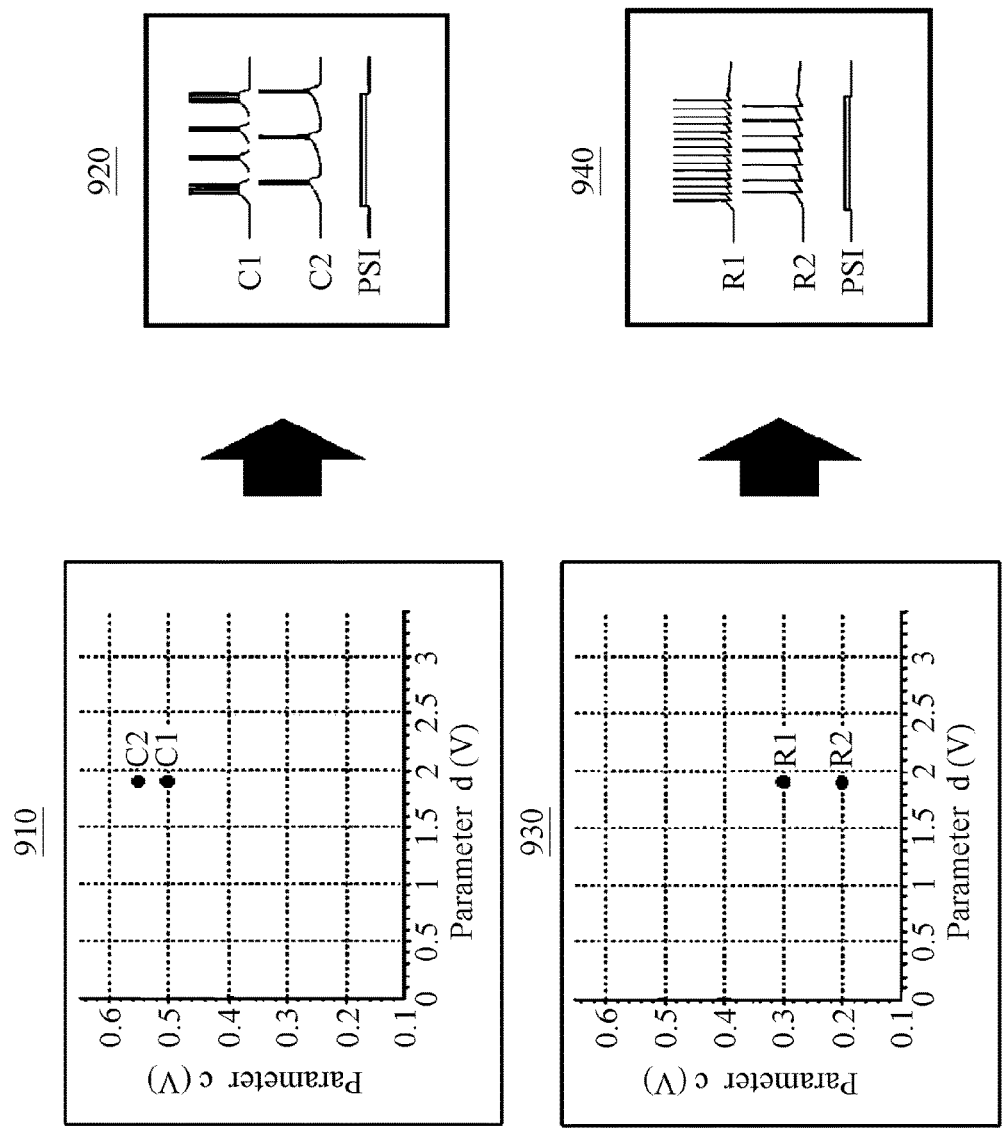
FIG. 9 illustrates an example of inputs and outputs of an analog circuit.

FIG. 9 illustrates an example of inputs and outputs of an analog circuit. Referring to FIG. 9, graphs 910 and 930 show inputs of an analog circuit, and graphs 920 and 940 show outputs of the analog circuit in response to the corresponding inputs.

The graph 910 includes inputs C1 and C2, and the graph 930 includes inputs R1 and R2. Each of the inputs C1, C2, R1, and R2 corresponds to a different combination of parameters c and d as indicated by the vertical and horizontal axes of the graphs 910 and 930. The parameters c and d correspond to the input signals c and d described with reference to FIG. 8. The graph 920 includes a waveform generated by the input C1 and a waveform generated by the input C2, and the graph 940 includes a waveform generated by the input R1 and a waveform generated by the input R2. Signals PSI shown in the graphs 920 and 940 correspond to the input signal Post Synaptic Input described with reference to FIG. 8.

Referring to the graph 920, a chattering type waveform is generated by the input C1 and the input C2, and a detailed form of the waveform is adjusted based on a value of the input C1 and a value of the input C2. Furthermore, referring to the graph 940, a regular type waveform is generated by the input R1 and the input R2, and a detailed form of the waveform is adjusted based on a value of the input R1 and a value of the input R2. Thus, a category of the stimulus signal and a detailed form of the stimulus signal are adjusted by the input signals c and d in the example of FIG. 8.

Figure 10:
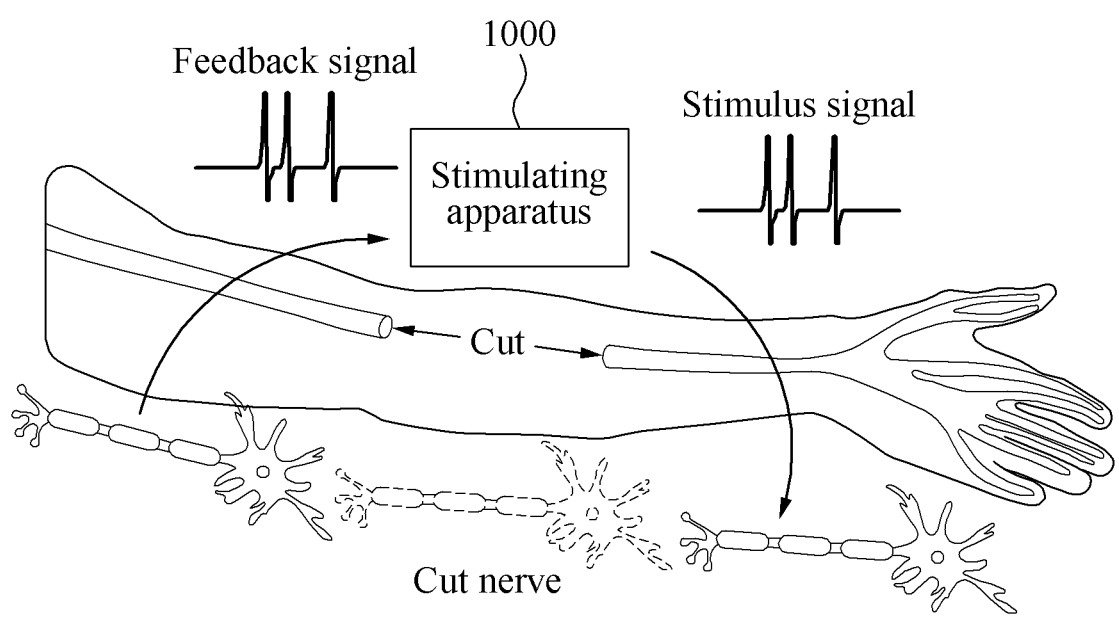
FIG. 10 illustrates an example of a stimulating apparatus used to assist a cut nerve.

FIG. 10 illustrates an example of a stimulating apparatus used to assist a cut nerve. Referring to FIG. 10, a stimulating apparatus 1000 detects a feedback signal from a cut nerve before a cut in the nerve, and applies a stimulus signal to the cut nerve after the cut in the nerve. The detected feedback signal corresponds to a "motor nerve activation" neural response, and the stimulating apparatus 1000 generates a stimulus signal corresponding to a "motor nerve activation" physical function by referring to a pre-constructed data set. As described above, in a case in which there is a cut nerve, the stimulating apparatus 1000 is used to assist the cut nerve. When the stimulating apparatus 1000 is implemented as a cut nerve assistance device, the stimulating apparatus 1000 is implanted under a skin of a patient in a periphery of the cut nerve, and a surface of the stimulating apparatus 1000 may include a titanium material that is relatively biocompatible with the human body.

Figure 11:
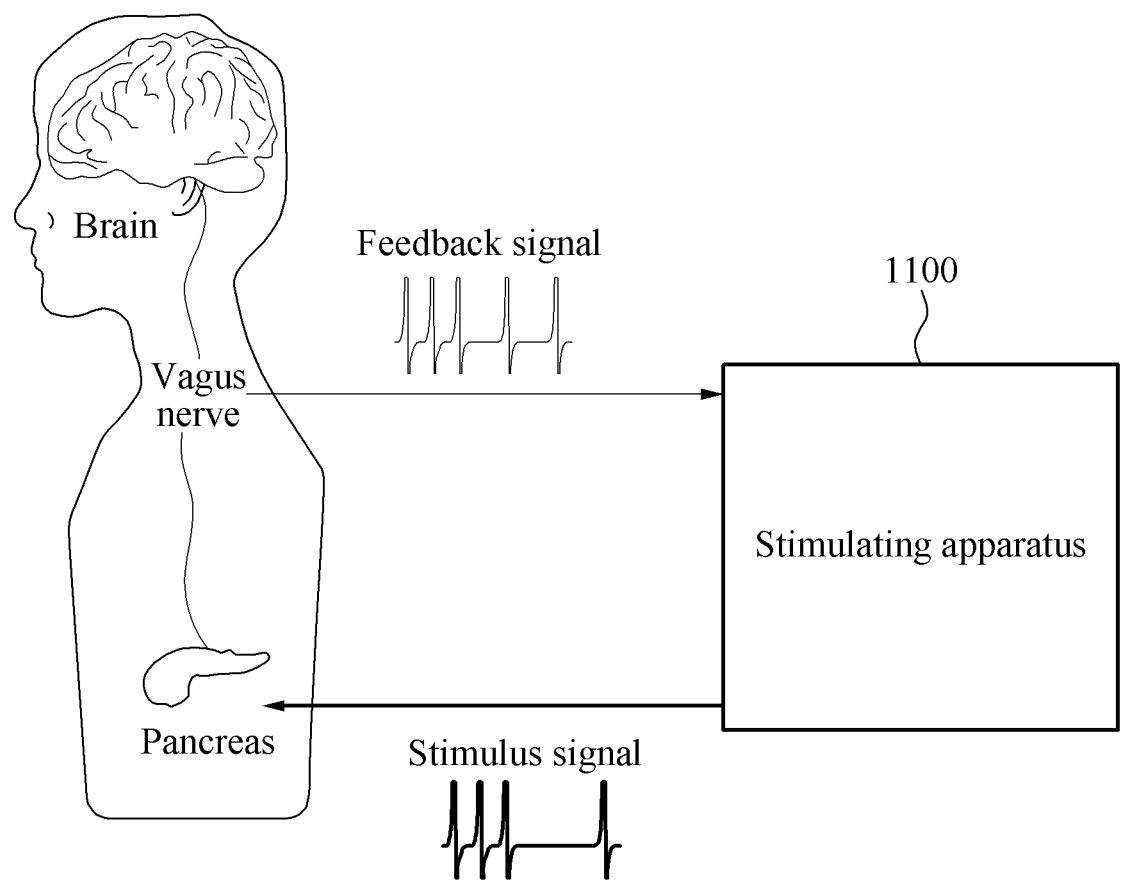
FIG. 11 illustrates an example of a stimulating apparatus used as an electronic medicine device.

FIG. 11 illustrates an example of a stimulating apparatus used as an electronic medicine device. Referring to FIG. 11, a stimulating apparatus 1100 detects a feedback signal from a vagus nerve, and applies a stimulus signal to a pancreatic region. The detected feedback signal corresponds to a "food ingestion" neural response, and the stimulating apparatus 1100 generates a stimulus signal corresponding to an "insulin secretion" physical function by referring to a pre-constructed data set. As described above, the stimulating apparatus 1100 is used to activate a predetermined physical function. When the stimulating apparatus 1100 is implemented as an electronic medicine device, the stimulating apparatus 1100 is ingested into a human body or implanted into a human body, and a surface of the stimulating apparatus 1100 may include a titanium material that is relatively biocompatible with the human body.

Figure 12:
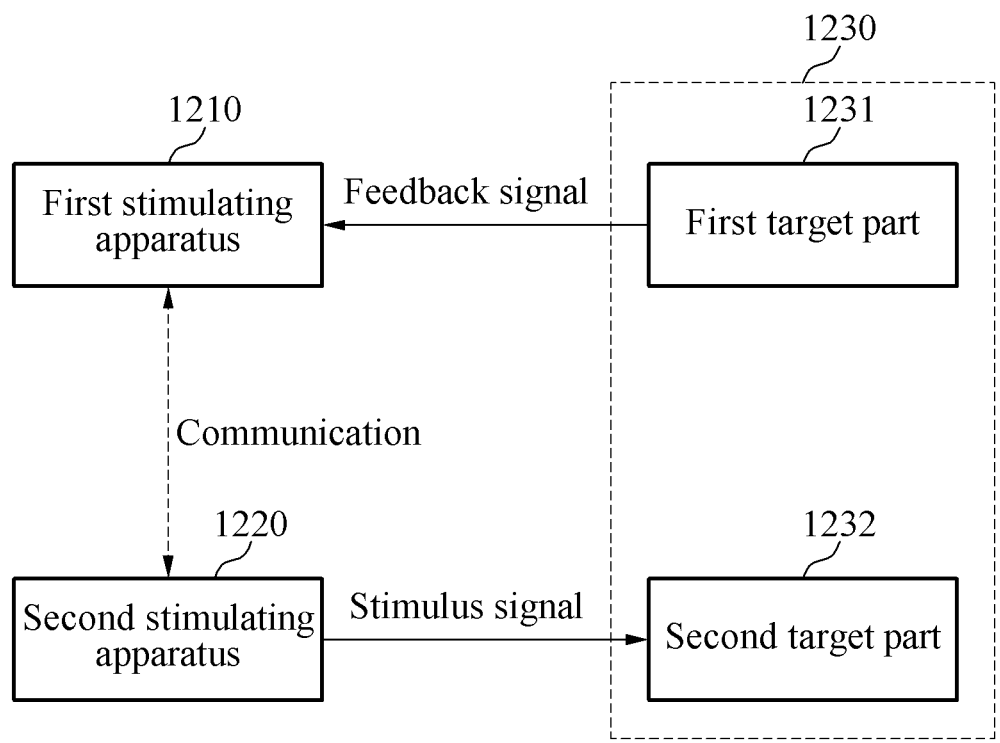
FIG. 12 illustrates an example of a cooperative operation between a plurality of stimulating apparatuses.

FIG. 12 illustrates an example of a cooperative operation between a plurality of stimulating apparatuses. Referring to FIG. 12, a first stimulating apparatus 1210 detects a feedback signal from a first target part 1231 of a target 1230 to be stimulated, and a second stimulating apparatus 1220 applies a stimulus signal to a second target part 1232 of the target 1230. In one example, the first target part 1231 and the second target part 1232 are separated by a predetermined distance. In this example, the first stimulating apparatus 1210 and the second stimulating apparatus 1220 exchange desired information through communication. The first stimulating apparatus 1210 detects the feedback signal at an appropriate position, and the second stimulating apparatus 1220 applies the stimulus signal at an appropriate position. For example, the first stimulating apparatus 1210 transmits information related to the feedback signal detected from the first target part 1231 to the second stimulating apparatus 1220, and the second stimulating apparatus 1220 generates the stimulus signal based on the received information related to the feedback signal. The first stimulating apparatus 1210 and the second stimulating apparatus 1220 each include a communication module to perform communication. The first stimulating apparatus 1210 and the second stimulating apparatus 1220 may communicate directly with each other, or may communicate indirectly through an external device.

Figure 13:
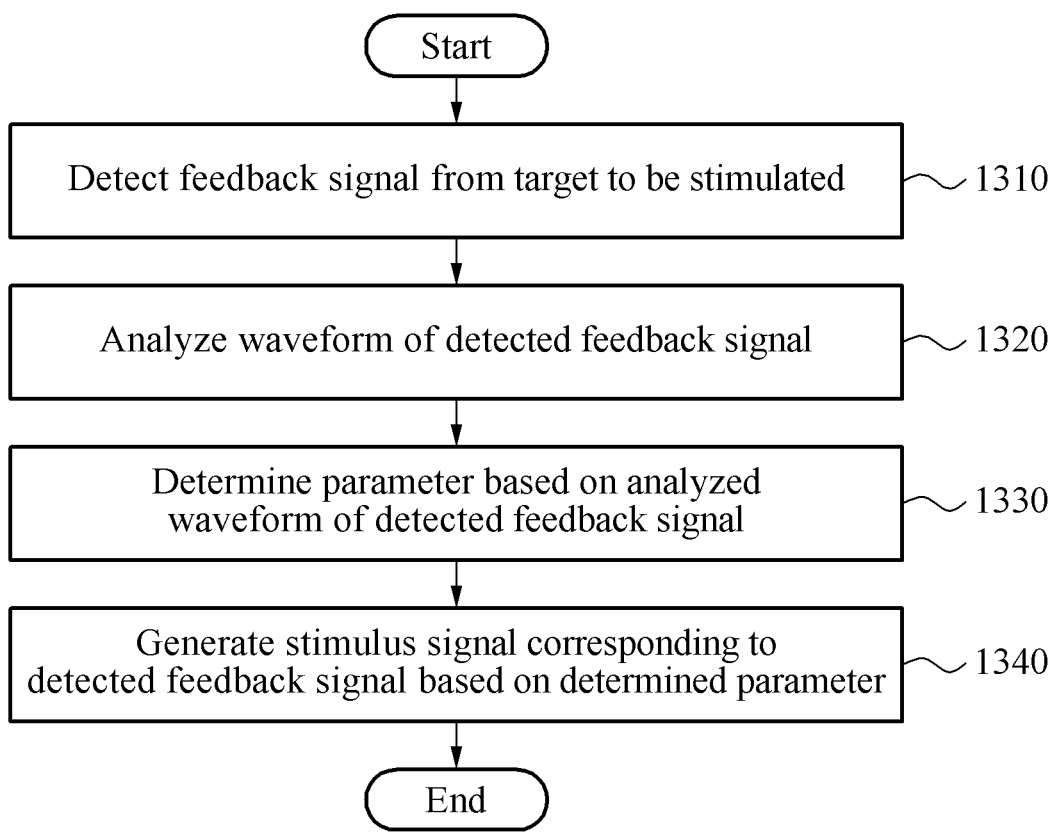
FIG. 13 is a flowchart illustrating an example of a stimulating method.

FIG. 13 is a flowchart illustrating an example of a stimulating method. Referring to FIG. 13, in operation 1310, a stimulating apparatus detects a feedback signal from a target to be stimulated. In operation 1320, the stimulating apparatus analyzes a waveform of the detected feedback signal. In operation 1330, the stimulating apparatus determines a parameter based on the analyzed waveform of the detected feedback signal. In operation 1340, the stimulating apparatus generates a stimulus signal corresponding to the detected feedback signal based on the determined parameter. The description provided above with respect to FIGS. 1 through 12 is also applicable to the stimulating method illustrated in FIG. 13, and thus a duplicate description will be omitted for conciseness.

Figure 14:
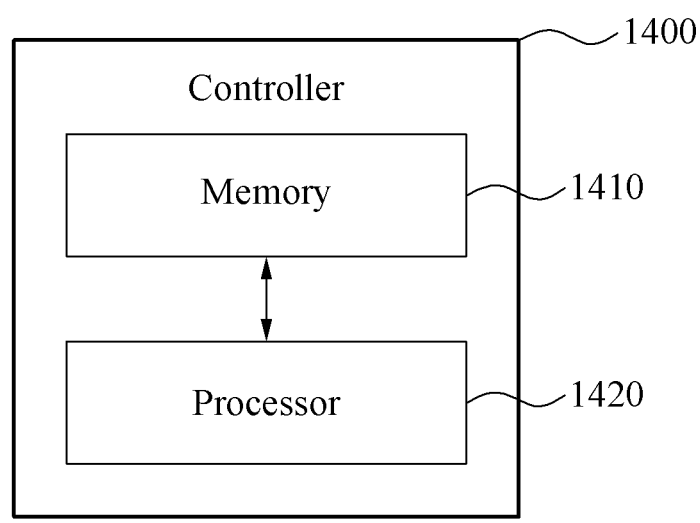
FIG. 14 is a block diagram illustrating an example of a controller of a stimulating apparatus.

FIG. 14 is a block diagram illustrating an example of a block diagram of a controller of a stimulating apparatus. Referring to FIG. 14, a controller 1400 includes a memory 1410 and a processor 1420, and may be used to implement the controller 220 of the stimulating apparatus 200 illustrated in FIG. 2, and to perform the operations 1320 and 1330 of the stimulating method illustrated in FIG. 13. The memory 1410 stores instructions that, when executed by the processor 1420, cause the processor 1420 to perform the operations performed by the controller 220 as described with respect to FIGS. 1-12, and to perform the operations 1320 and 1330 of the stimulating method illustrated in FIG. 13. The descriptions of FIGS. 1-13 are also applicable to FIG. 14, and thus will not be repeated here.

The stimulating apparatus 110 in FIG. 1, the stimulating apparatus 200, the feedback detector 210, the controller 220, the memory 230, the communication module 240, and the signal generator 250 in FIG. 2, the feedback detector 600, the high-cut filter 610, the medium frequency amplifier 620, the low-cut filter 630, the variable amplifier 640, and the analog-to-digital converter (ADC) 650 in FIG. 6, the signal generator 700, the analog circuit 710, the driver circuit 720, the operating electrode driver 730, the counter electrode driver 740, and the charge balancer 750 in FIG. 7, the analog circuit 800 in FIG. 8, the stimulating apparatus 1000 in FIG. 10, the stimulating apparatus 1100 in FIG. 11, the first stimulating apparatus 1210 and the second stimulating apparatus 1220 in FIG. 12, and the controller 1400, the memory 1410, and the processor 1420 in FIG. 14 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, filters, amplifiers, analog-to-digital converters, transistors, capacitors, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The method illustrated in FIG. 13 that performs the operations described in this application is performed by hardware components configured to perform the operations described in this application that are performed by the method. One or more of the operations of the method may be performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A stimulating apparatus comprising:
a feedback detector configured to detect a feedback signal from a target to be stimulated;
a controller configured to analyze a waveform of the detected feedback signal by determining features of the detected feedback signal based on a signal level, a duration, a number of peaks, and a number of clusters of the detected feedback signal, and determine a parameter using information associated with reference data of feedback signals, neural responses, and stimulus signals based on the analyzed waveform of the detected feedback signal, including identifying, by referring to a pre-constructed data set, a neural response corresponding to the detected feedback signal, the pre-constructed data set storing the information associated with the reference data of the feedback signals, the neural responses, and the stimulus signals; and a signal generator configured to generate a non-square analog wave stimulus signal corresponding to the detected feedback signal based on the determined parameter, wherein a waveform according to features of the stimulus signal is determined by the determined parameter, and wherein the non-square analog wave stimulus signal includes an irregular analog wave of a first frequency band and an irregular non-square pulse of a second frequency band.

2. The stimulating apparatus of claim 1, wherein the controller is further configured to determine a neural response indicated by the detected feedback signal based on the analyzed waveform of the detected feedback signal, and determine the parameter based on the determined neural response.

3. The stimulating apparatus of claim 2, wherein the controller is further configured to determine the neural response indicated by the detected feedback signal by obtaining the neural response indicated by the detected feedback signal from a data set storing the feedback signals and the neural responses mapped to the feedback signals based on the analyzed waveform of the detected feedback signal.

4. The stimulating apparatus of claim 3, wherein the feedback signals stored in the data set are obtained by exposing the target to environments that induce the neural responses stored in the data set.

5. The stimulating apparatus of claim 2, wherein the controller is further configured to determine the parameter by obtaining the stimulus signal corresponding to the determined neural response from a data set storing the neural responses and the stimulus signals mapped to the neural responses, and determine the parameter based on the obtained stimulus signal.

6. The stimulating apparatus of claim 1, wherein the controller is further configured to determine a category to which the detected feedback signal belongs among categories of neural signals, and analyze the waveform of the detected feedback signal by detecting an interval between peaks in the detected feedback signal.

7. The stimulating apparatus of claim 1, wherein the stimulus signal is effective to induce in the target a physical function corresponding to the stimulus signal in response to the stimulus signal being applied to the target.

8. The stimulating apparatus of claim 1, wherein the stimulus signal is configured to mimic a neural signal occurring in the target.

9. The stimulating apparatus of claim 1, wherein the signal generator comprises an analog circuit configured to output an analog signal corresponding to a waveform of the stimulus signal based on the determined parameter.

10. The stimulation apparatus of claim 9, wherein the analog circuit comprises capacitors and transistors, and the analog circuit is further configured to output the analog signal in response to an input signal corresponding to the determined parameter being applied to any one or any combination of any two or more of the capacitors and the transistors.

11. The stimulation apparatus of claim 10, wherein the capacitors comprise a first capacitor and a second capacitor, the first capacitor is configured to generate a signal in a-the first frequency band in the analog signal based on the input signal, and the second capacitor is configured to generate pulses having a frequency in a-the second frequency band on peaks of the signal in the first frequency based on the input signal.

12. The stimulating apparatus of claim 1, wherein the controller is further configured to determine the parameter to be effective to induce a predetermined physical function in the target, and the signal generator is further configured to generate the stimulus signal to be effective to induce the predetermined physical function in the target based on the determined parameter.

13. A stimulating method comprising:

detecting a feedback signal from a target to be stimulated;

analyzing a waveform of the detected feedback signal by determining features of the detected feedback signal based on a signal level, a duration, a number of peaks, and a number of clusters of the detected feedback signal;

determining a parameter using information associated with reference data of feedback signals, neural responses, and stimulus signals based on the analyzed waveform of the detected feedback signal, including identifying, by referring to a pre-constructed data set, a neural response corresponding to the detected feedback signal, the pre-constructed data set storing the information associated with the reference data of the feedback signals, the neural responses, and the stimulus signals; and generating a non-square analog wave stimulus signal corresponding to the detected feedback signal based on the determined parameter, wherein a waveform according to features of the stimulus signal is determined by the determined parameter, and wherein the non-square analog wave stimulus signal includes an irregular analog wave of a first frequency band and an irregular non-square pulse of a second pulse of a second frequency band.

14. The stimulating method of claim 13, further comprising determining a neural response indicated by the detected feedback signal based on the analyzed waveform of the detected feedback signal, wherein the determining of the parameter comprises determining the parameter based on the determined neural response.

15. The stimulating method of claim 14, wherein the determining of the neural response indicated by the detected feedback signal comprises obtaining the neural response indicated by the detected feedback signal from a data set storing the feedback signals and the neural responses mapped to the feedback signals based on the analyzed waveform of the detected feedback signal.

16. The stimulating method of claim 14, wherein the determining of the parameter further comprises:

determining the parameter by obtaining a stimulus signal corresponding to the determined neural response from a data set storing the neural responses and the stimulus signals mapped to the neural responses; and determining the parameter based on the obtained stimulus signal.

17. The stimulating method of claim 13, wherein the analyzing of the waveform of the detected feedback signal comprises:

determining a category to which the detected feedback signal belongs among categories of neural signals; and detecting an interval between peaks in the detected feedback signal.

18. The stimulating method of claim 13, wherein the generating of the stimulus signal comprises inputting an input signal corresponding to the determined parameter into an analog circuit configured to output an analog signal corresponding to a waveform of the stimulus signal in response to the input signal.

19. The stimulating method of claim 13, wherein the determining of the parameter comprises determining the parameter to be effective to induce a predetermined physical function in the target, and the generating of the stimulus signal comprises generating the stimulus signal to be effective to induce the predetermined physical function in the target based on the determined parameter.

20. A non-transitory computer-readable medium storing instructions that, when executed by a processor, cause the processor to perform the stimulating method of claim 13.

21. A stimulating apparatus comprising:

a feedback detector configured to detect a feedback signal from a target to be stimulated;

a memory configured to store instructions;

a processor configured to execute the instructions stored in the memory to configure the processor to:

analyze the detected feedback signal to determine a stimulus signal to be applied to the target by determining features of the detected feedback signal based on a signal level, a duration, a number of peaks, and a number of clusters of the detected feedback signal, and determine a parameter, to be used to generate the stimulus signal, from information associated with reference data of feedback signals, neural responses, and stimulus signals, including identifying, by referring to a pre-constructed data set, a neural response corresponding to the detected feedback signal, the pre-constructed data set storing the information associated with the reference data of the feedback signals, the neural responses, and the stimulus signals; and a signal generator configured to generate the stimulus signal based on the parameter, wherein a waveform of the stimulus signal is determined to be a non-square analog wave by the parameter, and wherein the non-square analog wave stimulus signal includes an irregular analog wave of a first frequency band and an irregular non-square pulse of a second frequency band.

22. The stimulating apparatus of claim 21, wherein the processor is further configured to:

analyze the detected feedback signal to determine a neural response indicated by the detected feedback signal, and determine the stimulus signal to be effective to induce in the target a physical function corresponding to the neural response in response to the stimulus signal being applied to the target.

23. The stimulating apparatus of claim 22, wherein the processor is further configured to determine the neural response and the stimulus signal by referring to a data set storing the feedback signals and corresponding neural responses, physical functions, and the stimulus signals mapped to the feedback signals.

24. The stimulating apparatus of claim 21, wherein the processor is further configured to determine a first parameter related to a waveform of the stimulus signal, and a second parameter related to a level of the stimulus signal, and the signal generator is further configured to generate the stimulus signal based on the first parameter and the second parameter.

25. The stimulating apparatus of claim 21, wherein the processor is further configured to:

analyze a waveform of the detected feedback signal to determine a neural response indicated by the detected feedback signal, in response to the neural response indicating a need to change a hormone level in the target, determine, as the stimulus signal, a first stimulus signal having a waveform different from the waveform of the detected feedback signal, the waveform of the first stimulus signal being effective to change the hormone level in the target in response to the first stimulus signal being applied to the target, and in response to the neural response indicating a motor nerve is to be actuated in the target, determine, as the stimulus signal, a second stimulus signal having a waveform substantially the same as the waveform of the detected feedback signal, the waveform of the second signal being effecting to activate the motor nerve in the target in response to the second stimulus signal being applied to the target.

\* \* \* \* \*